United States Patent
Baath

(10) Patent No.: US 9,453,725 B2
(45) Date of Patent: Sep. 27, 2016

(54) METHOD AND APPARATUS FOR QUANTITATIVE MEASUREMENT OF SURFACE ACCURACY OF AN AREA

(71) Applicant: QSO INTERFEROMETER SYSTEMS AB, Halmstad (SE)

(72) Inventor: Lars Baath, Eldsberga (SE)

(73) Assignee: QSO Interferometer Systems AB, Halmstad (SE)

( * ) Notice: Subject to any disclaimer, the term of this patent is extended or adjusted under 35 U.S.C. 154(b) by 0 days.

(21) Appl. No.: 14/765,353

(22) PCT Filed: Feb. 10, 2014

(86) PCT No.: PCT/SE2014/050159
§ 371 (c)(1),
(2) Date: Aug. 3, 2015

(87) PCT Pub. No.: WO2014/126526
PCT Pub. Date: Aug. 21, 2014

(65) Prior Publication Data
US 2016/0003614 A1    Jan. 7, 2016

(30) Foreign Application Priority Data
Feb. 14, 2013   (SE) ...................... 1330009

(51) Int. Cl.
G01N 21/95    (2006.01)
G01N 21/88    (2006.01)
G01B 11/30    (2006.01)
G01N 21/956   (2006.01)

(52) U.S. Cl.
CPC .......... *G01B 11/303* (2013.01); *G01B 11/306* (2013.01); *G01B 11/30* (2013.01); *G01N 21/88* (2013.01); *G01N 21/8806* (2013.01); *G01N 21/95* (2013.01); *G01N 21/956* (2013.01)

(58) Field of Classification Search
CPC ....... G01B 11/30; G01N 21/88; G01N 21/95

USPC ............... 356/237.1–241.6, 242.1–243.8, 356/426–431, 600–640
See application file for complete search history.

(56) References Cited

U.S. PATENT DOCUMENTS

| | | | |
|---|---|---|---|
| 4,334,780 A | 6/1982 | Pernick | |
| 4,754,282 A * | 6/1988 | Edelblute | G01S 3/802 342/378 |

(Continued)

FOREIGN PATENT DOCUMENTS

| | | |
|---|---|---|
| JP | 2012-093200 A | 5/2012 |
| JP | 2012-093316 A | 5/2012 |

(Continued)

OTHER PUBLICATIONS

International-Type Search Report for corresponding Swedish Patent Application No. SE 133009-0 dated Oct. 29, 2013.

(Continued)

*Primary Examiner* — Tri Ton
*Assistant Examiner* — Jarreas C Underwood
(74) *Attorney, Agent, or Firm* — Renner, Otto, Boisselle & Sklar, LLP

(57) ABSTRACT

A method for quantitative measurement of surface accuracy of an area is provided. This comprises directing a monochromatic flat light wave towards a predefined surface area, recording an image of the reflected light with a camera and lens system focused on said surface area, and deducing surface accuracy parameters from the recorded image. The method is characterized in that said surface accuracy parameters are determined by obtaining a Fourier transform of the recorded image. Then, fitting predetermined Fourier components to a Fourier spectrum of said Fourier transform, wherein said Fourier components are determined along the major and across the minor elongation axes of the Fourier transform as at least a large Gaussian component, and a peak of the spectrum. Followed by, determining surface accuracy parameters of said surface area from said Fourier components.

8 Claims, 3 Drawing Sheets

(56) References Cited

U.S. PATENT DOCUMENTS

| | | | |
|---|---|---|---|
| 4,846,578 A | | 7/1989 | Morita et al. |
| 4,873,434 A | | 10/1989 | See et al. |
| 5,917,191 A | | 6/1999 | Cheng |
| 5,999,884 A | * | 12/1999 | Kriegshauser .......... G01V 3/28 702/7 |
| 6,084,671 A | | 7/2000 | Holcomb |
| 6,782,342 B2 | * | 8/2004 | LeGore ................. G01N 23/05 250/282 |
| 7,286,218 B2 | * | 10/2007 | Tiemeyer ............... G01N 21/21 356/237.2 |
| 8,446,640 B2 | * | 5/2013 | Dyck ................... H04N 1/0473 347/238 |
| 2005/0046870 A1 | | 3/2005 | Lex |
| 2007/0236686 A1 | | 10/2007 | Kishioka |
| 2012/0107971 A1 | | 5/2012 | Birang et al. |

FOREIGN PATENT DOCUMENTS

| | | |
|---|---|---|
| JP | 2012-137484 A | 7/2012 |
| WO | 91/16601 A1 | 10/1991 |

OTHER PUBLICATIONS

International Search Report for corresponding International Application No. PCT/SE2014/050159 dated May 27, 2014.

International Preliminary Report on Patentability for corresponding International Application No. PCT/SE2014/050159 dated May 19, 2015.

Dhanasekar et al., "Evaluation of surface roughness based on monochromatic speckle correlation using image processing", Precision Engineering, vol. 32, No. 3, Jul. 2008, pp. 196-206.

Pino et al., "Measurement of the roughness surface using the normalized autocorrelation function of the fields of the texture of speckle pattern", Proc. SPIE vol. 8413, Speckle 2012: V International Conference on Speckle Metrology, Sep. 11, 2012, 6 pages.

Lehmann et al., "Comparison of Conventional Light Scattering and Speckle Techniques Concerning an In-Process Characterisation of Engineered Surfaces", CIRP Annals—Manufacturing Technology, vol. 49, No. 1, 2000, pp. 419-422.

Goodman, "Some properties of speckle from smooth objects", Optical Engineering, vol. 49, No. 6, Jun. 2010, pp. 068001-068009.

* cited by examiner

METHOD AND APPARATUS FOR QUANTITATIVE MEASUREMENT OF SURFACE ACCURACY OF AN AREA

This application is a national phase of International Application No. PCT/SE2014/050159 filed Feb. 10, 2014 and published in the English language, and claims priority to Application No. SE 1330009-0 filed Feb. 14, 2013.

TECHNICAL FIELD

The embodiments herein relates to a method for in-situ optical quantitative measurement of surface accuracy of an area during polishing process.

BACKGROUND

Surface modifications, especially polishing, are a required process in many industrial production areas. These include:
- Automotive, e.g. polishing of moulds for plastic parts such as boot lids and light covers and lenses.
- Engine parts such as cam axes.
- Medical implants, e.g. the surface of artificial hip joints.
- Optics such as injection moulds for safety glasses and contact lenses.

Such polished surfaces can be several square meters in size and require a surface accuracy of 1 micrometer or less. Today, the sample is moved from the polishing process to a laboratory where the surface is measured at small areas at a time in a time-consuming process. Furthermore, most of the polishing is done manually, where the manual polisher establishes the quality by looking at the tool/mould, whereas the automatic procedure using robot or laser has, in general, to be checked by taking the tool/mould out of the process chamber.

In order to check the surface accuracy, several methods are known in the art.

U.S. Pat. No. 6,084,671 discloses a method and apparatus for surface analysis using Gaussian beam profiles. A Gaussian beam is shaped with a lens system and illuminates a surface. The reflected light is distorted by surface irregularities. The reflected beam is then observed through a series of spatial filters which basically remove the original Gaussian beam shape. The measured beam with difference in residual beam shape is the recorded with a camera. This solution requires that the surface is illuminated by a very specific beam pattern in the form a Gaussian shape. Further, the illumination of the surface is uneven over the surface in that the edges of the studied area is less intensely illuminated than the center and any statistical measure of the surface structure is therefore biased towards the center.

US 2005/0046870 disclose a method for characterizing surfaces by illuminating it at an angle to show shadowgraph of larger structure on the surface. This solution describes and discusses geometrical reflections only. It does not relate to illuminating polished surfaces with monochromatic light. Further, the illumination is not directed perpendicularly to the surface.

US 2012/107971 discloses a polishing pad assembly for a chemical mechanical polishing apparatus. The polishing pad has a polishing surface and a surface opposite the polishing surface for attachment to a platen, and a solid light-transmissive window formed in the polishing pad. The light-transmissive window is more transmissive to light than the polishing pad. The light-transmissive window has a light-diffusing bottom surface. This solution requires a chemical transparent top layer over the surface to produce interference with the surface reflected wave. This is a single spot measurement instrument and technique which measures interference between two overlapping surfaces.

U.S. Pat. No. 4,873,434 discloses a scanning optical microscope which comprises a source of optical radiation and means for focusing radiation from the source into an interrogating spot on a surface under examination. The spot is deflected about a point on the surface, and the surface topography is measured by measuring the amplitude and/or phase of the radiation reflected from the surface at the spot position. This technique measures one spot at a time. Each spot is handled separately and does not give any direct quantitative analysis of a larger area.

U.S. Pat. No. 5,917,191 discloses a method for measuring surface topography characterized by making multiple scans of the surface with a laser scanning unit and utilizing the multiple scans to create representations of the surface's topography. The surface topography data can also be used to calculate the compressive or tensile stress caused by a thin film applied to the surface of a semiconductor wafer. The apparatus of the solution scans a laser beam across a surface in an x direction, and detects displacements of a reflected portion of the laser beam in a z direction. A pair of photo detectors is used to translate z direction displacements of the reflected beam into analog signals which are digitized and input into a microcomputer for analysis. The multiple scans of the surface are preferably accomplished by placing the work piece on a pedestal which can be rotated to various angular positions. This technique is scanning point by point to give point topographic data. It neither describes nor teaches quantitative analysis over a large area simultaneously.

SUMMARY

It is therefore an object of the embodiments herein to provide a method for quantitative measurements of surface quality during polishing processes, wherein the method would eliminate the drawbacks of the prior art.

The embodiments herein relates to a method and apparatus for determining quantitative accuracy of a surface, wherein a beam of parallel monochromatic light is sent perpendicularly towards the surface of a sample. Quantitative parameters defining the surface topography are then deduced by simultaneously recording the intensity of the reflected light at each pixel in a camera image focused with a camera lens on the surface area under investigation. The area intensity image is then Fourier-transformed from the surface aperture dimensions to scattering angle dimensions. Image surface parameters are then calculated from the intensity Fourier transform and coupled to quantitative surface parameters.

The embodiments herein describes a method and apparatus for in-situ optical quantitative measurement of surface accuracy of an area during polishing process, wherein a monochromatic flat light wave is directed towards a predefined surface area and the image of the reflected light is recorded with a camera and lens system focused on the surface area. The flat light wave is directed perpendicularly or at an angle less than 6 degrees towards the surface. Further, the camera and lens system may be positioned perpendicularly to or at an angle less than 6 degrees towards the surface. The difference in angle between the reflected light entering the camera and the optical axis of the camera and lens system may be less than 6 degrees.

The surface accuracy parameters are then deduced from the recorded image. The surface accuracy parameters may be determined with a Fourier transform of the recorded image, predetermined Fourier components are fitted to the Fourier spectrum of the surface area, and surface accuracy parameters are determined from the Fourier components. Such Fourier components may then be determined along the major and across the minor elongation axes of the Fourier transform as a large Gaussian component; the peak of the spectrum; a wide Gaussian component as foundation to the peak; and component peak outside the central maximum.

Further components may be fitted to the major and minor axes as the quota of the major and minor axes of large Gaussian components; the direction of the major axis; and the direction of the component peak outside the maximum centre. Surface accuracy parameters may then be deduced such as the large Gaussian component along the major axis divided with the central peak maximum, thus defining the quality of the polishing; the wide Gaussian component near the peak divided by the large Gaussian component defining the gloss of the surface; the large Gaussian component along the major elongation axis divided with the large Gaussian component along the minor axis defining the symmetry of the surface; the direction of the major axis showing the direction of structural lines of the surface, and the size of a component peak outside the centre maximum peak indicating structural lines.

The method and apparatus are defined in number of wavelengths rather than geometrical size, and are not limited to a specific optical wavelength even though this is used as example.

The method and apparatus have been verified and tested for the cases where the focus pixel area is less than 100 wavelengths in diameter, and the surface observing imaging area is larger than 4000 wavelengths in diameter. These are not theoretical limitations but rather practical due to present limits on number of pixels of camera.

Embodiments herein are especially useful for determining surface parameters over a large area. It is robust and mounted to make measurements inside a process chamber. The working distance is long, 70-800 mm, which is much longer than for microscope objective systems used presently.

The industrial use ranges from decision on process route and method in automatic polishing for automatic, medical and optical industrial tools, moulds and products; to objective decision making in manual polishing processes. The apparatus can be mounted on a robot arm, outside a laser process chamber or on the floor in manual polishing workshops. The method comprises taking a single image of a large part, in the case discussed below 4×4 mm, of the surface area and is therefore quick and much more insensitive to vibrations compared to single point measurements and interferometry instruments. The total surface area can then also be measured by stepping over the total area in steps of, in the case discussed below, 2-4 mm.

The surface accuracy may be defined as how the surface is topographically deviating from being flat in the same plane as the light wave.

Some specific advantages of some embodiments herein are:

Long working distance: can be placed 70-800 mm from the target area;
Large surface simultaneously: fast measurement;
Quantitative data over large area as feedback to the polishing process.

BRIEF DESCRIPTION OF THE DRAWINGS

Embodiments will now be described by way of example with reference to the accompanying drawings, of which.

DETAILED DESCRIPTION

Figure 1:
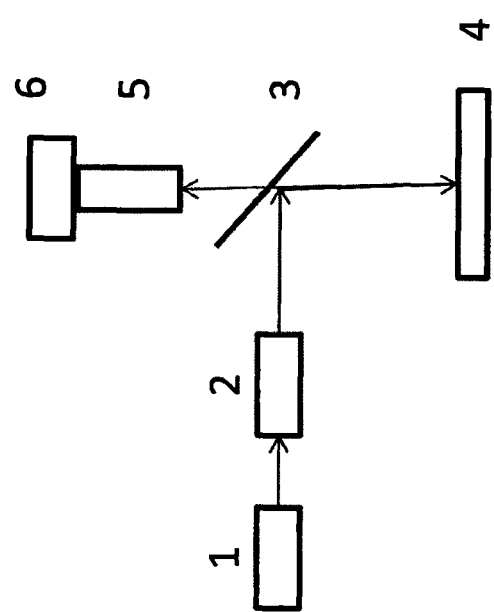
FIG. 1 illustrates an apparatus according to embodiments herein.

FIG. 1 depicts a monochromatic light source (laser or laser diode) 1 at wavelength λ emits light into a beam expander 2. It may here be noted that a beam expander expands the laser beam so that the central area where the measurements are taken can be considered as having the same phase and amplitude on a flat plane, i.e. there is a monochromatic flat light wave hitting the surface. The flat wave front light from the beam expander is reflected from a beam splitter 3 to an object surface 4. The light is reflected from the surface through the beam splitter into a focusing lens 5 and recorded with a camera 6. The camera used in the example is a CCD camera; having a camera lens of 75 mm. The diameter of the focusing spot at the surface in the example is 2 micrometer.

Figure 2:
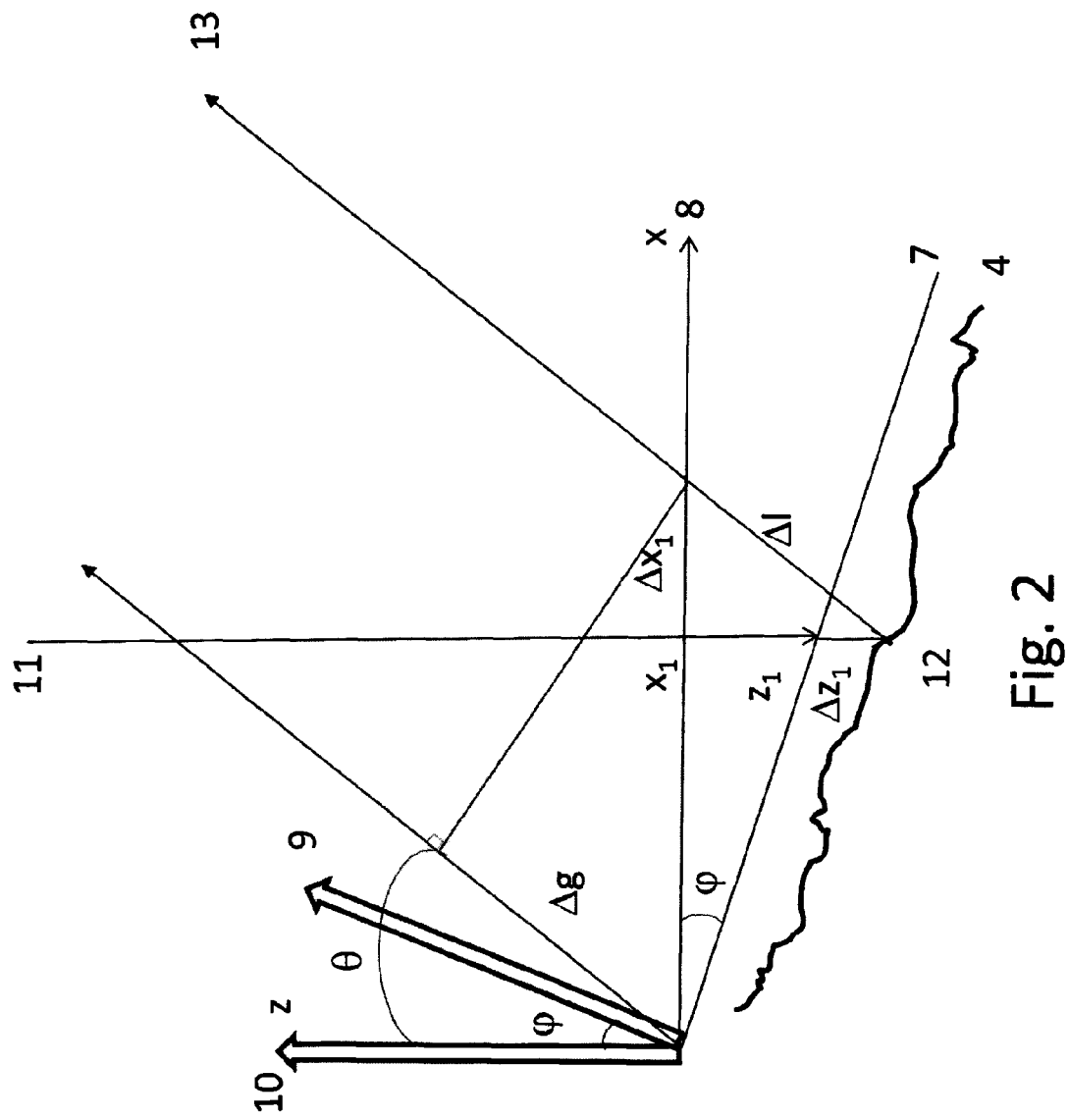
FIG. 2 illustrates a geometry of the system according to embodiments herein.

The geometry of the system is shown in FIG. 2. The object surface 4 is limited to inside of the focusing area spot. The surface has a reference plane 7 and the incoming flat wave plane is represented with a line 8. The normal 9 to the surface reference plane 7 has a tilt angle φ to the normal 10 of the incoming flat wave 8. The incoming light from direction 11 at $x=x_1$, hits the object surface 4 at point 12 $x_1$, $z_1+\Delta z_1$. The phase of the light 13 emitted from point 12 in a direction θ to the normal 10 of the incoming light wave plane 8 is calculated. The phase center is a position (x=0, z=0) in the coordinate system defined by the incoming flat wave 8 and the normal 10 at a position where it crosses the surface reference plane 7.

Figure 3:
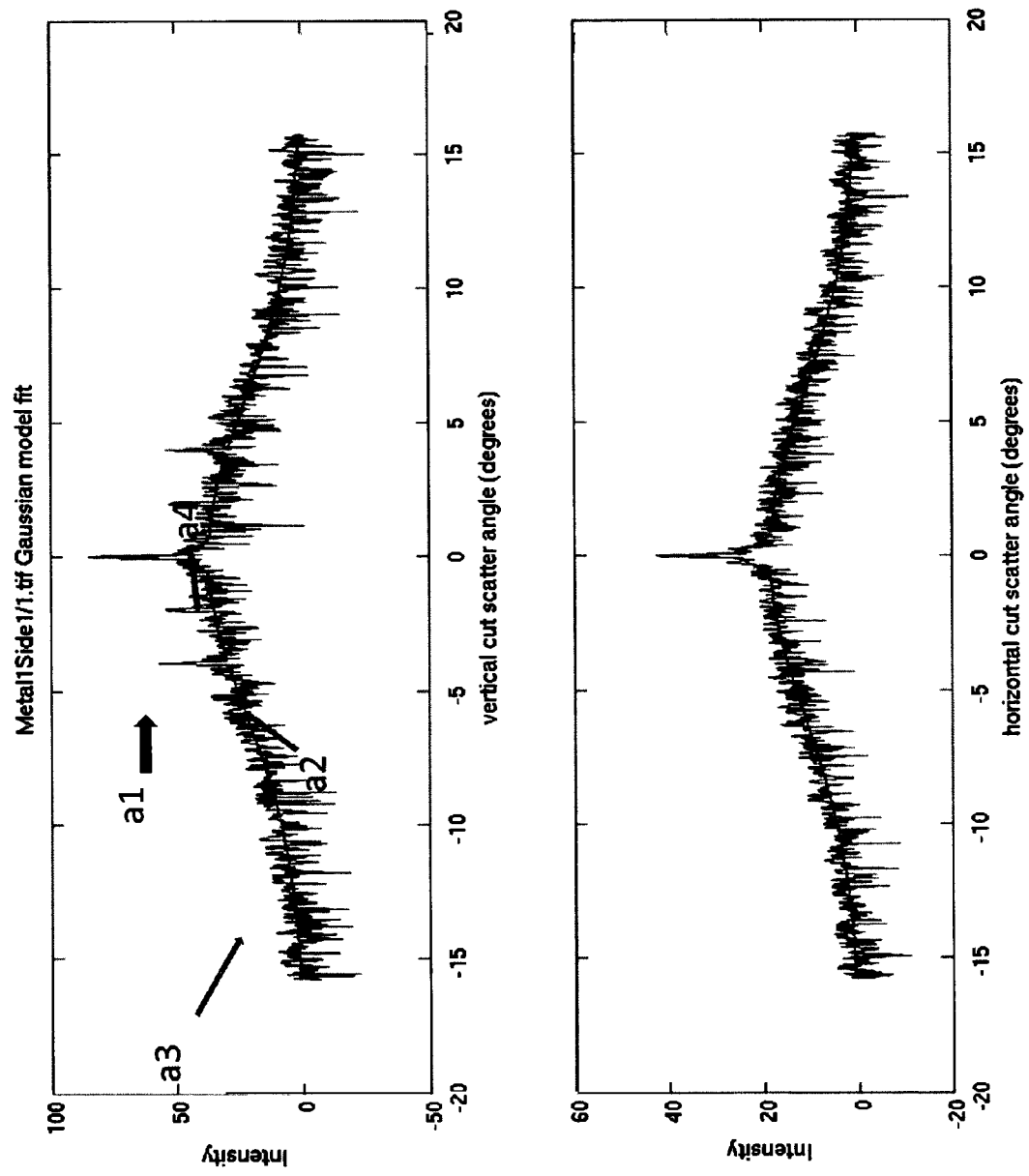
FIG. 3 illustrates the intensity of the Fourier transform of the image.

FIG. 3 shows the intensity of the Fourier transform of the image in a cut through the major axis of the elliptical Gaussian noise distribution of the transform. The notations a1-a4 are components discussed below.

The phase of the incoming light at z=0 is zero at all points x along the object surface. The discussion below is concentrated to the light scatter inside one focusing spot, i.e. same as one recorded pixel on the CCD. We also assume that the emitting source at position $(x_1, z_1+\Delta z_1)$ is much smaller than one wavelength and thus works as a spherical scatter point of the incoming wave.

The light coming in through x=x1 and emitted at the angle θ is delayed by:

$$\Delta L = z_1 + \Delta z_1 + \Delta l$$

Where $\Delta z_1$ is the offset of the surface from a plane and $$z_1 = x_1 \times \tan(\varphi)$$

$$\Delta l = \frac{z_1 + \Delta z}{\cos(\Theta)}$$

In addition, there is a geometrical path difference $\Delta g$, between the wave emitted from position (x=0, z=0) and the wave emitted from the surface and passing z=0 at $x=x_1+\Delta x_1$. This path can be calculated as $$\Delta g = (x_1 + \Delta x_1) \times \sin(\Theta)$$

Where $$\Delta x_1 = (z_1 + \Delta z_1) \times \tan(\Theta)$$

The phase difference between the wave coming in through and emitted at the phase reference position (x=0, z=0) and the corresponding wave at (x=$x_1$, z=$z_1$+$\Delta z_1$) at the line going through position (x=0, z=0) perpendicular to the emitting angle θ is therefore $$\delta(x) = 2\pi \frac{\Delta L(x) - \Delta g(x)}{\lambda}$$

This function can be further extended by introducing a curvature of the focal surface f(x) to become $$\delta(x) = 2\pi \frac{\Delta L(x) - \Delta g(x) + f(x)}{\lambda}$$

The complex voltage of the signal reflected at position (x=$x_1$, z=$z_1$+$\Delta z_1$) is $$V_1(x_1) = A_1 e^{-i\delta_1(x_1)}$$

where $A_1$ is the amplitude of the signal.

This is readily extended to two dimensions (x, y). The focal area is tilted at angles ($\phi_x$, $\phi_y$) and the offset from a plane is the two dimensional function $\Delta z(x, y)$ The complex voltage of the reflected light from the focusing area in the direction ($\theta_x$, $\theta_y$) is then the coherent sum of all complex voltages as:

$$V(\text{focalarea}) = \Sigma_x \Sigma_y V(x,y)$$

The intensity emitted in direction ($\theta_x$, $\theta_y$) from the focal area S(X, Y) is $$I_{X,Y}(\alpha, \beta) = \langle V(X,Y) * V(X,Y)^* \rangle_T$$

T is the averaging time for the intensity, X, Y is the position of the focal area on focal plane over the sample, α is the zenith angle and β is the azimuth angle of the emitted light.

In the same manner we now define the tilt angles $\phi_x$ and $\phi_y$ as zenith χ and azimuth ξ angles to the normal of the focal plane. We also set the focal plane to be parallel to the incoming wave front.

According to some embodiments herein, the camera is angled to look onto the sample in the same direction as the light from the beam expander, as shown in FIG. 1. The zenith angle is then α=0, or ($\theta_x$=0, $\theta_y$=0). In this case the phase offset for the position (x, y) in the plane where the x-axis in the direction of the azimuth angle $\phi_y$ can be written as:

$$\delta(x, y) = 2\pi \frac{x * \tan(\varphi_x) + \Delta z(x, y) + f(x, y)}{\lambda}$$

The complex voltage emitted from the focal area is then $$V(\text{focalarea}) = \Sigma_x \Sigma_y A(x, y) e^{-i2\pi \frac{x*\tan\varphi_x + \Delta z(x,y) + f(x,y)}{\lambda}}$$

Assuming that the material is the same at each pixel x, y, and the surface variations Δz and f are small over the focal area, then A is constant over the focal area and this becomes:

$$V(\text{focalarea}) = A * \Sigma_x \Sigma_y e^{-i2\pi \frac{x*\tan\varphi_x + \Delta z(x,y) + f(x,y)}{\lambda}}$$

The intensity emitted from the focal area at position X, Y can then be written as $$I_{X,Y} = \left\langle A^2 \Sigma_x \Sigma_y e^{-i2\pi \frac{x*\tan\varphi_x + \Delta z(x,y) + f(x,y)}{\lambda}} * \Sigma_x \Sigma_y e^{i2\pi \frac{x*\tan\varphi_x + \Delta z(x,y) + f(x,y)}{\lambda}} \right\rangle_T$$

Here $A^2$ is the intensity reflected by a perfect mirror and the second term is the attenuation of this by out of phase interference depending on the tilt angle $\phi_x$, the surface variation Δz(x, y) and the form factor f(x, y). Note that the interference also can be constructive resulting in Speckle radiation from the focal surface area.

Assuming that the material is the same over the whole sample and that the amplitude A thus can be considered the same everywhere, the direct returned intensity for each focal area is only dependent on the local surface geometry:
1. tilt angle $\phi_x$,
2. surface variation Δz(x, y), and
3. form factor f(x, y).

The focal area is the same as the Airy disc of the camera objective. The camera lens system is constructed so that an Airy disc is imaged onto one CCD pixel. In this case therefore the observed intensity image of the sample is a direct measure of the relative local surface geometry of the focal areas of the sample. Nearby pixels with the same intensity form image structure, caused by e.g. a similar tilt angle.

The embodiments herein are not limited to zenith angle of zero degrees. A small angle between the incoming and reflected beams is possible if this angle is small compared to the diffraction angle of size scale under consideration. In practice, this means that the difference in angle between the illuminating monochromatic light and the camera lens system optical axis should be less than 6 degrees.

Example

A tool surface is being polished by a machine or a human. The polishing process requires measurements of the surface area representing the surface roughness in order to be able to determine the way to proceed with the polishing process in order to reach a predefined smoothness. In this case, the target in blocks of 4×4 mm with 2000×2000 pixels at focal resolution of 2000 nm is studied. The light is emitted from a laser diode at the wavelength of 635 nm.

An image of the 4×4 mm surface area on the target surface is recorded with a CCD camera with 2000×2000 gray scale pixels. The image in position (i, j) at the surface is $I_{i,j}(X, Y)$ is Fourier transformed and the absolute value of the Fourier transform is stored as dB in a matrix:

$$S_{i,j}(u,v) = 20 * \log_{10}(\|F(I(X,Y))\|)$$

Here, u and v are the spatial frequency in the X and Y directions, respectively.

$S_{i,j}(u, v)$ is a two-dimensional spatial spectrum of the surface area geometry. This is now studied and the following surface structure parameters are extracted as:
1. The central peak (S1) at (u=0, v=0) is the total reflected intensity of the area.
2. There is a large bulge (S3), which corresponds to the randomly distributed intensity variations.
3. The peak S1 has a pedestal (S2), which corresponds to the nearby pixels having similar intensity.
4. Isolated peak (S4) correspond to a large-scale linear structure.

5. S3 is elliptical (asymmetry), indicating that the intensity is more ordered in one direction along the structure angle ϕ.

We can now connect these intensity structure parameters to the surface geometry parameters above.

A perfect mirror with tilt angle $\phi_x=0$, $\Delta z=0$, and f=0 everywhere would have a single peak S1 only.

Linear lines, i.e. caused by the previous honing step, would show as isolated peaks S4.

A one-directional polishing would show more random features in one direction compared to the elliptical distributed noise S3 with major axis position angle $\phi_{gauss}$.

A rough surface would have a large variation in tilt angles $\phi_x$ and show a large Gaussian distribution S3.

A surface where the tilt angles $\phi_x$ are similar for most focal areas would show smaller S3 and larger S2. This would look like a glossy surface, but not quite a mirror.

Also, the gloss can be more in one direction and more mirror-like in the other at an angle $\phi_{gloss}$.

Finally, when the focal area geometry becomes flat, i.e. both $\Delta z$ and f are small ($<\lambda/10$), the surface would turn into a mirror.

The surface parameters are then further reduced as cuts are made through the Fourier transform S(u,v) along the major axis position angle $\phi_{gauss}$ and perpendicular to this. Gaussian profiles are fitted to the features described above and denoted as:

major axis cut: a1p, a2p, a3p, and a4p (FIG. 3);
minor axis cut: a1m, a2m, a3m.

The maximum intensity in the center of the transform S is denoted as amax. Note that these values are in dB. The structural parameters are then calculated as:

1. amax−a3p=Gaussian noise part, i.e. the amount of wide band noise compared to the total returned intensity.
2. (amax−a3p)/(amax−a3m)=the asymmetry of the Gaussian noise.
3. $\phi_{gauss}$=the angle of the asymmetry structure.
4. a4p−a3p=the amount of structural lines compared to Gaussian noise.
5. a2p−a3p=gloss.

Then, these parameters can either be mapped over the sample surface, or used individually for 4×4 mm spot tests of the sample.

The parameters can then be fed back to the polishing process to determine subsequent polishing steps.

To perform the method actions in the apparatus for determining quantitative accuracy of a surface, the apparatus may in some embodiments comprise or be connectable to a processing circuitry, which may also be referred to as processing module or processor. The processing circuitry may be configured to perform the image processing and analysis steps of the method actions as described in the embodiments herein.

The embodiments for determining quantitative accuracy of a surface may be implemented through one or more processors, such as, e.g. the processing circuitry comprised in or connectable to the apparatus depicted in FIG. 1, together with computer program code for performing the functions and actions of the embodiments herein. The program code mentioned above may also be provided as a computer program product, for instance in the form of a data carrier carrying computer program code or code means for performing the embodiments herein when being loaded into the processing circuitry. The computer program code may e.g. be provided as pure program code in the processing circuitry or on a server and downloaded to the processing circuitry. The carrier may be one of an electronic signal, optical signal, radio signal, or computer readable storage medium, such as, e.g. electronic memories like a RAM, a ROM, a Flash memory, a magnetic tape, a CD-ROM, a DVD, a Blueray disc, etc.

Thus, the apparatus may further comprise or be connectable a memory, which may be referred to or comprise one or more memory modules or units. The memory may be arranged to be used to store executable instructions and data to perform the methods described herein when being executed in the processing circuitry. Those skilled in the art will also appreciate that the processing circuitry and the memory described above may refer to a combination of analog and digital circuits, and/or one or more processors configured with software and/or firmware, e.g. stored in the memory, that when executed by the one or more processors such as the processing circuitry perform the method as described above. One or more of these processors, as well as the other digital hardware, may be included in a single application-specific integrated circuit (ASIC), or several processors and various digital hardware may be distributed among several separate components, whether individually packaged or assembled into a system-on-a-chip (SoC).

Thus, a computer program, comprising instructions which, when executed on at least one processor, e.g. the processing circuitry described above, cause the at least one processor to carry out the method for determining quantitative accuracy of a surface as described above is presented. Also, a carrier containing the computer program, wherein the carrier is one of an electronic signal, optical signal, radio signal, or computer readable storage medium, is presented.

The embodiments herein are not limited to the above described preferred embodiments. Various alternatives, modifications and equivalents may be used. Therefore, the above embodiments should not be construed as limiting.

The invention claimed is:

1. A method for quantitative measurement of surface accuracy parameters of an area, comprising:
    directing a monochromatic flat light wave towards a predefined surface area;
    recording an image of the reflected light with a camera and lens system focused on said surface area;
    deducing surface accuracy parameters from the recorded image;
    wherein said surface accuracy parameters are determined as follows:
        obtaining a two-dimensional spatial spectrum of the surface area geometry by a Fourier transform of the recorded image;
        fitting predetermined Fourier components in a major axis cut along the major elongation axis of an elliptical Gaussian noise distribution in the two-dimensional spatial spectrum;
        fitting predetermined Fourier components in a minor axis cut across the minor elongation axis of the elliptical Gaussian noise distribution in the two-dimensional spatial spectrum;
        determining surface accuracy parameters of said surface area from said Fourier components.

2. The method of claim 1, wherein said monochromatic flat light wave is directed perpendicularly or at an angle less than 6 degrees towards said surface area.

3. The method of claim 1, wherein said camera and lens system is arranged perpendicularly or at an angle less than 6 degrees towards said surface area.

4. The method of claim 1, wherein the difference in angle between said reflected light and the optical axis of said camera and lens system is less than 6 degrees.

5. The method of claim 1, wherein the focus pixel area is less than 100 wavelengths in diameter.

6. The method of claim 1, wherein the surface observing imaging area is larger than 4000 wavelengths in diameter.

7. The method of claim 1, wherein the light is at optical or infrared wavelengths of 300-1500 nanometers.

8. An apparatus for quantitative measurement of surface accuracy of an area, said apparatus comprising:
- a source of light for producing a beam of light directed along an optical path;
- a beam expander arranged along the optical path downstream from the light source;
- a positioning means for positioning a material in the optical path downstream from the beam expander;
- an imaging detector, arranged along the optical path downstream from the material, for detecting the reflected beam;

wherein said apparatus further comprise a processor configured to determine surface accuracy parameters as follows:
- obtain a two-dimensional spatial spectrum of the surface area geometry by a Fourier transform of the recorded image;
- fit predetermined Fourier components in a major axis cut along the major elongation axis of an elliptical Gaussian noise distribution in the two-dimensional spatial spectrum
- fit predetermined Fourier components in a minor axis cut across the minor elongation axis of the elliptical Gaussian noise distribution in the two-dimensional spatial spectrum; and determine surface accuracy parameters of said surface area from said Fourier components.

* * * * *